United States Patent [19]

Bollinger et al.

[11] 4,384,996

[45] May 24, 1983

[54] NOVEL CYCLOSPORINS

[75] Inventors: Pietro Bollinger, Bottmingen; Johann J. Bölsterli, Buus; Hans Kobel, Basel, all of Switzerland

[73] Assignee: Sandoz Ltd., Basel, Switzerland

[21] Appl. No.: 337,485

[22] Filed: Jan. 6, 1982

[30] Foreign Application Priority Data

Jan. 9, 1981 [GB] United Kingdom ............... 8100566
Jan. 9, 1981 [GB] United Kingdom ............... 8100567

[51] Int. Cl.³ .......................................... C07C 103/52
[52] U.S. Cl. ...................... 260/112.5 R; 260/112.5 S
[58] Field of Search .................. 260/112.5 R, 112.5 S

[56] References Cited

U.S. PATENT DOCUMENTS

| | | | |
|---|---|---|---|
| 4,108,985 | 8/1978 | Rüegger et al. | 260/112.5 R |
| 4,117,118 | 9/1978 | Härri et al. | 260/112.5 R |
| 4,210,581 | 7/1980 | Rüegger et al. | 260/112.5 R |
| 4,220,641 | 9/1980 | Traber et al. | 260/112.5 R |
| 4,288,431 | 9/1981 | Traber et al. | 260/112.5 R |
| 4,289,851 | 9/1981 | Traber et al. | 260/112.5 R |

FOREIGN PATENT DOCUMENTS 1491509  11/1977  United Kingdom.

OTHER PUBLICATIONS

Wenger, "European Patent Application", A20 034 567, 4-24-81.

*Primary Examiner*—Delbert R. Phillips
*Assistant Examiner*—F. T. Moezie
*Attorney, Agent, or Firm*—Gerald D. Sharkin; Robert S. Honor; Thomas O. McGovern

[57] ABSTRACT

Novel cyclosporins having an -Allylgly- residue in the 2-position and/or a -(D)-Ser- residue in the 8-position and process for their production. The novel cyclosporins are useful as pharmaceuticals, e.g. as immunosuppressive and anti-inflammatory agents.

9 Claims, No Drawings

NOVEL CYCLOSPORINS

The present invention relates to novel cyclosporins, processes for their production, their use as pharmaceutically active agents and pharmaceutical compositions containing them.

The cyclosporins comprise a class of structurally distinctive, cyclic, poly-N-methylated undecapeptides having valuable pharmacological, in particular immunosuppressive and anti-inflammatory activity. They include the naturally occurring cyclosporins, e.g. cyclosporins A, B, C, D and G, as well as chemically modified derivatives thereof, such as the corresponding dihydrocyclosporins (see e.g. U.S. Pat. Nos. 4,117,118, 4,210,581 and 4,108,985 as well as DOS 28 19 094 and 29 41 080). The cyclosporins A, B, C, D and G are illustrative of the class and may conveniently be represented by the general formula I,

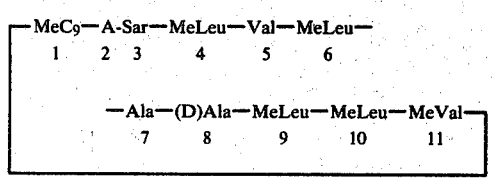

wherein "MeC$_9$" represents the so-called "C$_9$-amino acid" residue of formula II,

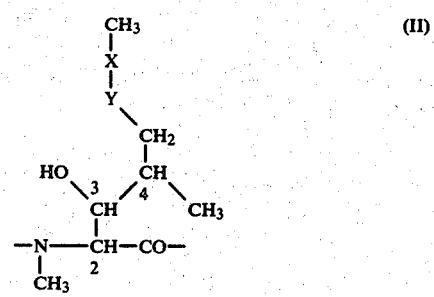

in which the positions 2, 3 and 4 have the configurations S,R and R respectively, —X—Y— is —CH=CH— (trans), and A is, for cyclosporin A, -α-Abu-;
for cyclosporin B, -Ala-;
for cyclosporin C, -Thr-;
for cyclosporin D, -Val-; and
for cyclosporin G, -NorVal-.

[Throughout the present specification and claims, amino acid residues referred to by abbreviation, e.g. -Ala-, -Sar-, -MeVal-, -NorVal- etc . . . are, in accordance with conventional practice, to be understood as having the (L)-configuration unless otherwise indicated. Residue abbreviations preceded by "Me" represent N-methylated residues. The individual residues of the cyclosporin molecule are numbered, as in the art, clockwise and starting with the residue -MeC$_9$- in position 1. The same numbering-system is used to indicate the position of individual residues throughout the present specification and claims.]

In the case of dihydrocyclosporins —X—Y— of the -MeC$_9$- residue (formula II) is —CH$_2$—CH$_2$—. In, for example, the iso-cyclosporins, the -MeC$_9$- residue is linked to the —CO— group of the adjacent -MeVal- in position 11, via its O-atom at the 3-position instead of the N-atom at the 2-position.

Until recently the only known method for the production of cyclosporins was by fermentation technique and by chemical modification of the obtained cyclosporin fermentation products. A total-synthetic method for the production of cyclosporins is however now available. This method, developed by R. Wenger, is described in Japanese Patent Application No. 020779/1981, European Patent Application No. 81810043.0 (Publication No. 0034567) and U.S. application Ser. No. 299,103, filed Sept. 3, 1981, the contents of which are incorporated herein by reference.

A key-feature of the total-synthetic method, is the provision for the first time of a means for obtaining the "C$_9$-amino acid" (in both cis- and trans-, and in dihydroform), the corresponding [2R,3S,4S]-enantiomers, and the N-desmethyl derivatives of these compounds in stereochemically pure form, none of these compounds having previously been known in isolated or isolable state.

In accordance with the total-synthetic method, these novel compounds are employed, generally in protected or activated form, as intermediates for the further synthesis of open-chain undecapeptide sequences which are finally cyclised to provide product cyclosporins. Undecapeptide synthesis and cyclisation are conducted in accordance with particular methods disclosed in the afforementioned references. The total-synthetic method accordingly provides a means of obtaining yet further cyclosporins, in which the "C$_9$-amino acid" is replaced by its afforementioned N-desmethyl derivative, enantiomers etc . . .

In accordance with the present invention it has now been found that novel cyclosporins may be obtained having valuable pharmacological properties, in which the residues at the 2- and/or 8-positions are replaced by amino acid residues of specified type.

Accordingly in its broadest aspect the present invention provides a cyclosporin having a β-vinylene-α-amino acid residue at the 2-position and/or a β-hydroxy-α-amino acid residue at the 8-position.

A suitable β-vinylene-α-amino acid residue is the -Allylgly- residue, i.e. of formula

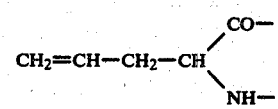

Suitable β-hydroxy-α-amino acid residues are -(D)-Ser- and -(D)-Thr-.

Preferred cyclosporins in accordance with the present invention are those of formula III,

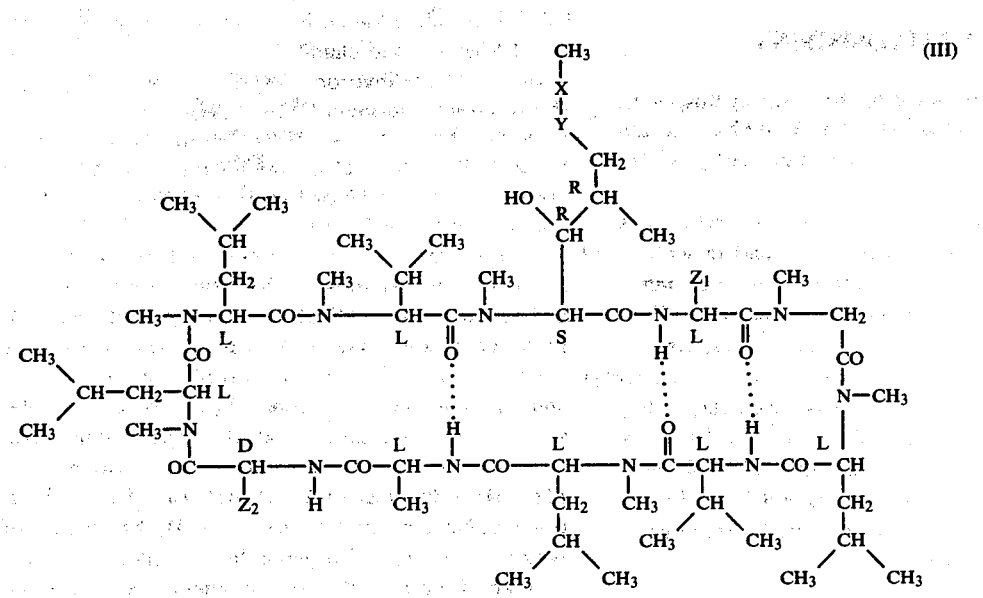

wherein
Z₁ is allyl or ethyl,
Z₂ is hydroxymethyl or, when Z₁ is allyl, Z₂ is methyl and —X—Y— is —CH=CH— (trans) or —CH₂—CH₂—.

Specific cyclosporins in accordance with the present invention are those of formula III wherein:

(i) Z₁ is allyl, Z₂ is methyl and —X—Y— is —CH=CH— (trans);
(ii) Z₁ is ethyl, Z₂ is hydroxymethyl and —X—Y— is —CH=CH— (trans); and
(iii) Z₁ is ethyl, Z₂ is hydroxymethyl and —X—Y— is —CH₂—CH₂—, these compounds being hereinafter referred to, throughout the specification and claims, as (i) "Allylgly②-cyclosporin"; (ii) "(D)-Ser⑧-cyclosporin" and (iii) "(D)-Ser⑧-dihydrocyclosporin" respectively.

Cyclosporins in accordance with the invention may be prepared by the total-synthetic method hereinbefore referred to. Further it has surprisingly been found that compounds of formula III above, wherein —X—Y— is —CH=CH— (trans) may also be prepared by a modification of the fermentation method described e.g. in the above mentioned U.S. Pat. No. 4,117,118 for the production of cyclosporin A, by addition of an amino acid precursor for -Allylgly- or -(D)-Ser- to the culture medium, -Allylgly- being incorporated into the cyclosporin molecule specifically at the 2-position and -(D)-Ser- specifically at the 8-position. Cyclosporins in accordance with the invention may further be subjected to chemical modification or interconversion by methods known in the art.

Accordingly in a further aspect the present invention also provides a process for the production of cyclosporins according to the invention, which process comprises:

(i) either (i a) removing O-protecting group(s) from a cyclosporin according to the invention in O-protected form; or (i b) cyclising a straight-chain undecapeptide having the sequence required to obtain a cyclosporin according to the invention and commencing with the residue at the 8-position of said cyclosporin as N-terminal, said undecapeptide being in unprotected or O-protected form and, when required, carrying out process step (i a): or (ii) for the production of a cyclosporin of formula III as defined above wherein —X—Y— is —CH=CH— (trans), cultivating a cyclosporin A producing fungus strain in contact with a nutrient medium containing (a) (L)- or (D,L)-allylglycine, or (b) (D)- or (D,L)-serine, or (c) a mixture of amino acids (a) and (b), and isolating the cyclosporin of formula III thus obtained from the culture medium; or (iii) chemically modifying a cyclosporin in accordance with the invention, e.g. obtained in accordance with (i a), (i b) or (ii) above, e.g. hydrogenating a cyclosporin of formula III, wherein —X—Y— is —CH=CH— (trans), Z₁ has the meaning given for formula III and Z₂ is hydroxymethyl, to obtain the corresponding cyclosporin of formula III wherein —X—Y— is —CH₂—CH₂— and Z₁ is ethyl.

Undecapeptides suitable for use in process step (i b) may be obtained analogously to the methods described in the above mentioned Japanese, European and U.S. patent applications Nos. 020779/1981, 81810043.0 and 299,103 respectively, e.g. in relation to flow-chart① thereof, by combination of the peptide sequence comprising residues 8 through 11 of the cyclosporin molecule with the sequence comprising residues 1 through 7 but with the desired substitution of residues at positions 2 and/or 8, e.g. substitution with -Allylgly- or -(D)-Ser- respectively. When a β-hydroxy-α-amino acid residue is present at position 8 this is suitably in O-protected form, e.g. in the form of the O-t-butyl derivative. The cyclisation of step (i b) is carried out using the particular techniques described in the said Patent Applications, with final removal of O-protecting groups when present, e.g. at the 8-position [step (i a)] in accordance with techniques known in the art of peptide chemistry. The general procedure is illustrated with particular reference to the synthesis of "(D)-Ser⑧-cyclosporin" in the following example 1 and the flowchart thereto.

The preferred fungus strain for use in the method of process step (ii) is the strain NRRL 8044 of the species *Tolypocladium inflatum* (Gams), a culture of which has been deposited with the U.S. Department of Agriculture (Northern Research and Development Division), Peoria, Ill., U.S.A. and is freely available to the public. A further culture of this strain has been deposited with the Fermentation Research Institute, Inage, Chiba City, Japan, under the code number FRI FERM-P No. 2796. The said strain was originally classified as belonging to the species *Trichoderma polysporum* (Link ex Pers.) and its morphological characteristics, as well as methods for the preparation and maintainance of pre- and sub-cultures are fully described e.g. in U.K. patent specification No. 1,491,509.

In accordance with the method of the invention the cyclosporin A producing strain is suitably maintained for a period of ca. 2 weeks at a temperature of ca. 27° C. in a culture medium such as described in the afforementioned U.K. patent specification No. 1,491,509, or as described in the following examples 2 and 3, in the presence of added (D)- or (D,L)-Serine or of added (L)- or (D,L)-allylglycine or of mixtures thereof. The amino acid precursor is suitably added in an amount of from about 1 to about 15 g, more preferably from about 4 to about 10 g and most preferably about 8 g/liter culture medium.

Following incubation the culture is harvested and the obtained cyclosporin of formula III, e.g. "(D)-Ser⑧- or Allylgly②-cyclosporin" extracted in accordance with known techniques, e.g. by comminution of conidia and mycelia, followed by extractive and/or absorptive isolation. The initially obtained, raw cyclosporin may thereafter be purified, e.g. chromatographically and/or by recrystallisation, in particular to effect separation from other cyclosporin contaminants, in particular from contaminating cyclosporins A, B, C, D and/or G.

Cyclosporins in accordance with this invention, e.g. obtained in accordance with process step (i a), (i b) or (ii) may, when required, subsequently be subjected to chemical modification in accordance with the techniques known in the art, in particular by hydrogenation, as in process step (iii), e.g. in the case of "(D)-Ser⑧-cyclosporin" to yield "(D)-Ser⑧-dihydrocyclosporin". When a β-vinylene-α-amino acid is present at the 2-position this will be simultaneously reduced, e.g. in the case of -Allylgly- to -NorVal-.

Hydrogenation may be carried out analogously to known methods for reducing naturally occurring cyclosporins, e.g. cyclosporins C and D, to their corresponding dihydro derivatives, for example by catalytic hydrogenation e.g. in accordance with the general methods disclosed in U.K. patent specification No. 1,567,201. Hydrogenation is suitably effected under neutral pH conditions, at temperatures of from about 20° to about 30° C. and at atmospheric or slightly elevated pressure, in the presence of a catalyst such as platinum or, preferably, paladium (e.g. paladium on charcoal) in the presence of an inert solvent or diluent. Suitable solvents include ethyl acetate and lower aliphatic alcohols such as methanol and isopropanol. The resultant hydrogenation product may be purified in known manner, e.g. by chromatography.

The following examples are illustrative of the process of the present invention. The following abbreviations are used:

| | |
|---|---|
| BOC | = t-butyloxycarbonyl |
| Bzl | = benzyloxycarbonyl |
| —(D)-Ser(O—tBu)— | = —(D)-Ser— in O—t.butyl-protected form. |
| —MeC$_9$— | = the residue of formula |

$$\begin{array}{c} CH_3 \\ \diagdown \\ CH \\ \parallel \\ CH \\ \diagdown \\ CH_2 \\ HO \diagdown \quad \mid \\ \quad \quad CH \\ \diagdown R \diagup R \diagdown \\ CH \quad \quad CH_3 \\ \mid \\ -N-CH_2-CO- \\ \mid \quad S \\ CH_3 \end{array}$$

| | |
|---|---|
| —MeDHC$_9$— | = the residue of formula |

$$\begin{array}{c} CH_3 \\ \mid \\ (CH_2)_3 \\ \mid \\ HO \diagdown \quad CH \\ \diagdown R \diagup R \diagdown \\ CH \quad \quad CH_3 \\ \mid \\ -N-CH_2-CO- \\ \mid \quad S \\ CH_3 \end{array}$$

EXAMPLE 1: Total synthesis of
"(D)-Ser⑧-cyclosporin"

(1a)

Boc-(D)-Ser(O-tBu)-MeLeu-MeLeu-MeVal-MeC$_9$-Abu-Sar-MeLeu-Val-MeLeu-Ala-Bzl

The title compound is prepared in accordance with the flow-chart shown on the following page, process steps (A) being carried out analogously to examples 1m to 1r, and process steps (B) identically to examples 1a to 1l, of the afforementioned Japanese, European and U.S. Patent Applications Nos. 020779/1981; 81810043.0 and 299,103.

(1b)

Boc-(D)-Ser(O-tBu)-MeLeu-MeLeu-MeVal-MeC$_9$-Abu-Sar-MeLeu-Val-MeLeu-Ala-OH 3.56 g of the title compound to example (1a) are dissolved in 70 ml ethanol, and 13.2 ml of 0.2 N aqueous NaOH added. The reaction mixture is allowed to stand for 16 hours at 0° C. The obtained clear solution is adjusted to pH5 by the addition of 1 N HCl and evaporated to dryness under vacuum at 40° C. The residue is taken up in 300 ml methylene chloride and 150 ml demineralised water and shaken. After separation of the organic phase the aqueous phase is shaken with a further 150 ml methylene chloride. The combined methylene chloride extracts are dried over Na$_2$SO$_4$, filtered through talc and the solvent is evaporated off under vacuum. The remaining product is purified chromatographically using 200 g silica gel (0.062-0.2 mm) with methylene chloride/15% methanol as eluant, and the eluate collected in 30 ml fractions.

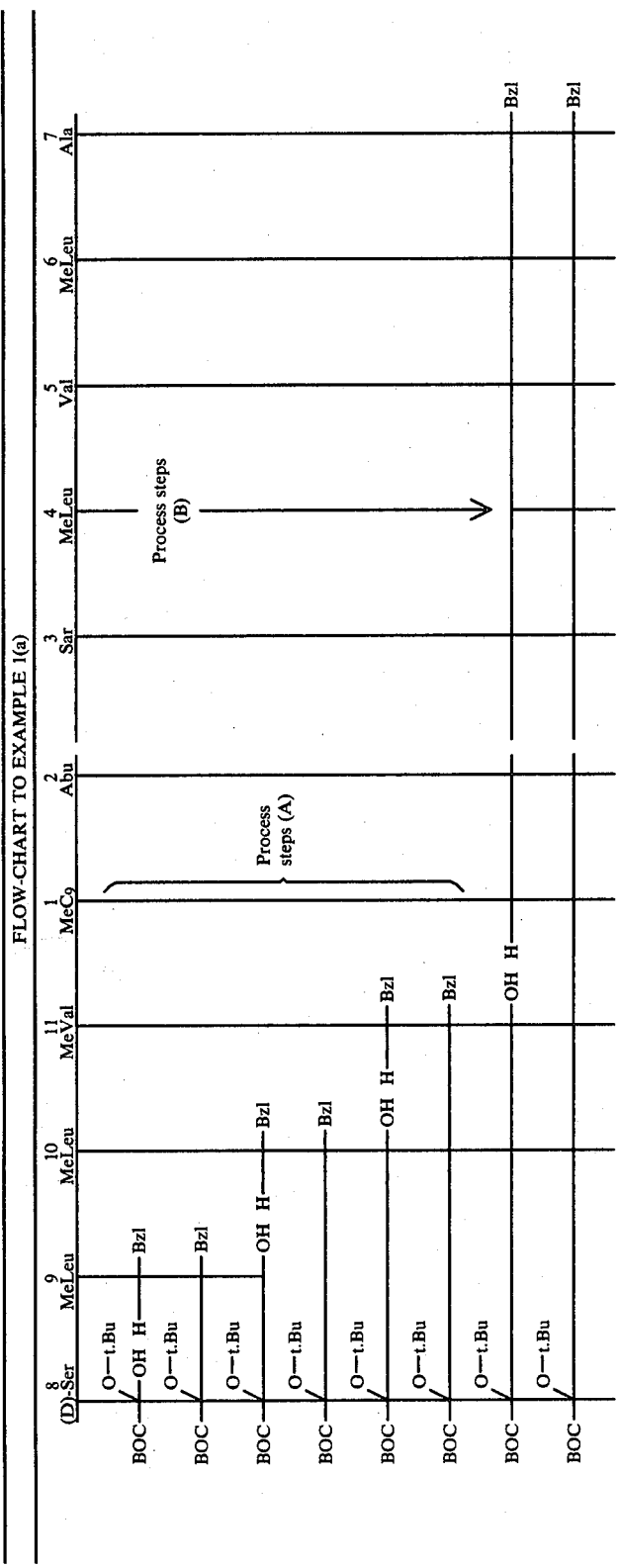

The title compound is recovered in pure form from fractions 13 to 45: $[\alpha]_D^{20} = -164.7°$; c=0.95 in CHCl$_3$.

(1c)
H-(D)-Ser-(O-tBu)-MeLeu-MeLeu-MeVal-MeC$_9$-Abu-Sar-MeLeu-Val-MeLeu-Ala-OH 1.9 g of the product of example (1b) in powder form are placed on 7 ml trifluoroacetic acid pre-cooled to −20° C., and dissolution effected by swirling. The solution is allowed to stand for 1¼ hrs. at −20° C. and poured through a separating funnel onto a mixture comprising ice, 200 ml saturated sodium bicarbonate solution and 300 ml methylene chloride. After shaking out, the aqueous phase should be nonacidic. After extracting twice with 300 ml methylene chloride, the combined organic phases are dried over Na$_2$SO$_4$, filtered off and evaporated. The residue is purified chromatographically on 150 g silica gel (0.063–0.2 mm) using methylene chloride/15% methanol as eluant and the eluate collected in 25 ml fractions. The title compound is recovered in pure form from fractions 25 to 90: $[\alpha]_D^{20} = -156°$; c=0.96 in CHCl$_3$.

(1d) "(D)-Ser(O-tBu)⑧-cyclosporin"

250 mg of the product of example (1c) are dissolved in 10 ml methylene chloride in a 50 ml flask provided with a calcium-chloride tube. 70.4 mg (0.077 ml) of N-methyl-morpholine dissolved in 1 ml CH$_2$Cl$_2$ are added, followed by 49.4 mg of propane phosphonic acid anhydride in 1 ml CH$_2$Cl$_2$ and the reaction mixture is stirred for 21 hrs. at 22° C. The obtained solution is diluted with 200 ml methylene chloride and shaken in a separating funnel with 100 ml sodium bicarbonate solution. The aqueous solution is again extracted with 100 ml methylene chloride, the organic phase dried over Na$_2$SO$_4$, filtered and the solvent evaporated. The residue is purified chromatographically on 150 g silica gel (0.063–0.2 mm) using methylene chloride/5% methanol as eluant, and the eluate collected in 25 ml fractions. The title compound is recovered in pure form from fractions 13 and 14.

(1e) "(D)-Ser⑧-cyclosporin"

345 mg of the product of example (1d) are dissolved in 2 ml trifluoroacetic acid and allowed to stand for 6 hrs. at 0° C. The reaction mixture is diluted with 150 ml methylene chloride and shaken with 100 ml ice/sodium bicarbonate solution in a separating funnel. The alkaline aqueous phase is separated off and re-extracted with 200 ml methylene chloride. The combined methylene chloride extracts are dried over Na$_2$SO$_4$ and filtered and the solvent fully evaporated off under vacuum. The residue is purified chromatographically on 250 g silica gel (0.063–0.2 mm) using methylene chloride/5% methanol as eluant and the eluate collected in 25 ml fractions. The title compound is recovered from fractions 42 to 52 in pure form.

EXAMPLE 2: Total synthesis of "(D)-Ser⑧-dihydrocyclosporin"

The title compound is prepared analogously to example 1, but with substitution of -MeDHC$_9$- for -MeC$_9$- at position 1 of the flow-chart to example (1a). The products at the last three steps of synthesis are characterised as follows:
(a)    Boc-(D)-Ser(O-tBu)-MeLeu-MeLeu-MeVal-MeDHC$_9$-Abu-Sar-MeLeu-Val-MeLeu-Ala-OH: $[\alpha]_D^{20} = -153°$ c=0.85 in chloroform.

(b)    H-(D)-Ser(O-tBu)-MeLeu-MeLeu-MeVal-MeDHC$_9$-Abu-Sar-MeLeu-Val-MeLeu-Ala-OH: $[\alpha]_D^{20} = -154.8°$ c=0.92 in MeOH.
(c)    "(D)-Ser(O-tBu)⑧-dihydrocyclosporin": $[\alpha]_D^{20} = -205°$ c=1.03 in CHCl$_3$.
(d)    "(D)-Ser⑧-dihydrocyclosporin": $[\alpha]_D^{20} = -241°$ c=1.0 in CHCl$_3$.

EXAMPLE 3: Micro-biological preparation of "(D)-Ser⑧-cyclosporin"

(2a)

10 Liters of a nutrient medium containing 50 g glucose; 8 g (D)-serine; 0.75 g K$_2$HPO$_4$; 0.5 g MgSO$_4$.7-H$_2$O; 0.1 g CaCl$_2$.6H$_2$O and 8 g ammonium maleate per liter is inoculated with 1 liter of a suspension of conidia and mycelia of the fungus strain NRRL 8044 taken from a pre-culture. The inoculated medium is filled in 100 ml portions into 100 Erlenmeyer flasks which are then incubated for 14 days at 27° on an agitator rotating at 180 r.p.m.. The mycelium is separated from the culture medium and extracted in a Turrax apparatus by crushing and stirring with 2×4.5 liters of 90% methanol. The crushed mycelium is separated from the solvent by suction-filtration and again treated 2x with 90% methanol as previously described. The combined filtrates are concentrated by evaporation under vacuum at a temperature of 40° C. until the vapour consists mainly of water alone. The obtained mixture is saturated with sodium chloride, extracted 3x using 3 liters of ethyl acetate at each extraction and the combined ethyl acetate solutions are dried over sodium sulfate and concentrated by evaporation under vacuum at a temperature of 40° C. The obtained residue is chromatographed on 440 g silica gel (silica gel "Merck", granulate size 0.04–0.063 mm) using chloroform/2% methanol as eluant, and is collected in 300 ml fractions. Fractions 41 to 53 are combined and evaporated under vacuum, and the residue (242 mg) is dissolved in 1 ml methanol and chromatographed in 125 μl portions on a high-pressure chromatographic column (RP8; diameter 8 mm; length 25 cm; temperature 70° C.; flow-rate 10 ml/min.; pressure 160 atm.) using water (39%)/methanol (5%)/acetonitrile (56%) as eluant, to yield 77 mg of pure "(D)-Ser⑧-cyclosporin": Rf: [chloroform/acetone (1:1)]=0.39.

(2b)

The pre-culture for the above process is produced as follows:

The spore and mycelium suspension used for inoculation is produced from a culture of the originally isolated strain NRRL 8044, cultivated for 21 days at 27° C. on an agar medium containing 20 g of malt extract, 20 g of agar, 4 g of yeast extract per liter of demineralised water. The spores of this culture are taken up in a physiological NaCl solution to give a final concentration of 5×10$^6$ spores/ml. 10 ml of this suspension are used for inoculation of 1 liter of a nutrient solution having the same composition as the culture medium of example (2a), with the exception of the (D)-serine component, and incubation is effected at 27° C. for 3 days on a rotatory shaker (200 r.p.m.). The fermentation solution is used as inoculating medium for the end culture.

EXAMPLE 4: Microbiological preparation of "Allylgly②-cyclosporin"

5 Liters of a nutrient medium containing 50 g glucose; 8 g (D,L)-allylglycine; 0.75 g K₂HPO₄; 0.5 g MgSO₄.7-H₂O; 0.1 g CaCl₂.6H₂O and 8 g ammonium maleate per liter is inoculated with 500 ml of a pre-culture of the fungus strain NRRL 8044 (produced in accordance with the method described in Example 2). The inoculated medium is filled in 100 ml portions into 50 Erlenmeyer flasks which are then incubated for 14 days at 27° C. on an agitator rotating at 180 r.p.m.. The mycelium is separated from the culture medium and extracted in a Turrax apparatus by crushing and stirring with 2×4.5 liters of 90% methanol. The crushed mycelium is separated from the solvent by suction-filtration and again extracted 2x with 90% methanol as previously described. The combined filtrates are concentrated by evaporation under vacuum at a temperature of 40° C. until the vapor consists mainly of water alone. The obtained mixture is saturated with sodium chloride, extracted 3x using 3 liters of ethyl acetate at each extraction and the combined ethyl acetate solutions are dried over sodium sulfate and concentrated by evaporation under vacuum at a temperature of 40° C.

The obtained residue is chromatographed on 320 g silica gel (silica gel "Merck", granule size 0.04–0.063 mm) with chloroform/2% methanol as eluant, and is collected in 0.5 to 1.0 liter fractions. Fractions 9 and 10, are combined and evaporated under vacuum to yield 2.9 g of an oily residue. The residue is chromatographed on 240 g silica gel using chloroform/1–2% methanol as eluant and collected in 20 ml fractions. Fractions 257–261 are combined and concentrated by evaporation under vacuum to yield a residue comprising 460 mg of semipure "Allylgly②-cyclosporin". This residue is dissolved in 1 ml methanol and passed in 125 μl portions through a high-pressure chromatographic column (RP8; diameter 8 mm, length 25 cm; temperature 70° C.; flow-rate 10 ml/min.; pressure 160 atm.) with water (35%)/methanol (15%)/acetonitrile (50%) as eluant, to yield 191 mg of enriched "Allylgly②-cyclosporin". Repetition of the final chromatographic step yields 87 mg "Allylgly②-cyclosporin" in purified form:

Rf:
[silica gel on glass, chloroform/acetone (1:1)]=0.69
[silica gel on glass, chloroform/methanol (9:1)]=0.66

Cyclosporins in accordance with the present invention exhibit valuable pharmacological, in particular immunosuppressive and anti-inflammatory activity as indicated in standard tests, e.g. as follows:

1. Immuno-suppressive activity:
   1.1 Local hemolysis in vitro in gel [R. I. Mishell and R. W. Dutton, J.Exp. Medicine, 126, 423–442 (1976)]. Cyclosporins in accordance with the invention inhibit haemolysis zones compared with untreated controls at concentrations of from 0.1 to 10.0 μg/ml.
   1.2 Lymphocyte stimulation test according to Janossy and Greaves [Clin. Exp. Immunol., 9, 483, (1971) and 10, 525 (1972)]:—Cyclosporins in accordance with the invention inhibit concanavalin A stimulated RNA-synthesis (inhibition of H³-thymidine assimilation), cell-proliferation and blastogenesis in mouse-spleen lymphocytes compared with untreated controls at concentrations of from 0.3 to 3.0 μg/ml.

2. Anti-inflammatory activity:
   Anti-inflammatory activity may be shown in the Freund's adjuvant arthritis latent period test in the rat and the Freund's adjuvant arthritis-therapy test in the rat on administration at appropriate dosages.

In view of their immuno-suppressive activity cyclosporins in accordance with the invention are useful for the prophylaxis and treatment of diseases and conditions requiring a reduction of the immune response. Thus they may be used to suppress the proliferation of lymphocytes and immunocytes e.g. in the treatment of autoimmune diseases or in preventing the rejection of transplants e.g. skin, bone-marrow and kidney transplants.

In view of their anti-inflammatory activity cyclosporins in accordance with the invention are useful for the treatment of inflammatory conditions, e.g. of arthritis and rheumatic diseases such as polyarthritis chronica progrediente.

In accordance with the foregoing the present invention provides, in a further aspect, a cyclosporin as hereinbefore defined, in particular a cyclosporin of formula III, for use as a pharmaceutical, i.e. for use in therapy and, in particular, for use in a method of treatment or prophylaxis as hereinbefore set forth.

For the above-mentioned uses the dose will, of course, vary depending on the mode of administration, the particular condition to be treated and the therapy desired. In general however, for immunosuppressive use, satisfactory results are obtained when administered at a daily dosage of from about 10 to 250 mg/kg animal body weight, conveniently administered in divided doses 2 to 3 times a day, or in retard form. For the larger mammals, the total daily dosage is in the range of from about 50 to 900 mg, e.g. from about 75 to 600 mg and preferably from about 200 to 400 mg, and dosage forms suitable for oral administration comprise from about 25 to 300 mg cyclosporin admixed with a solid or liquid pharmaceutical diluent or carrier.

As noted above, a suitable daily dosage for any specific cyclosporin will depend in particular on its relative potency of activity. For the preferred cyclosporins in accordance with the invention, "Allylgly②-cyclosporin" and "(D)-Ser⑧-cyclosporin", obtained results in tests 1.1 and 1.2 above are as follows:

| Test method | Concentration μg/ml | % inhibition compared with untreated control | |
|---|---|---|---|
| | | "Allylgly ②-cyclosporin" | "(D)-Ser ⑧-cyclosporin" |
| 1.1 | 0.1 | — | −48% |
| | 1.0 | — | −99% |
| | 10.0 | — | −100% |
| 1.2 | 0.3 | −23% | −51% |
| | 1.0 | −46% | −49% |
| | 3.0 | −68% | — |

In accordance with the foregoing the present invention also provides a pharmaceutical composition comprising a cyclosporin as hereinbefore defined, in particular a cyclosporin of formula III, together with a pharmaceutically acceptable diluent or carrier therefor.

Preferred pharmaceutical compositions according to the invention may be prepared by known methods e.g. in accordance with the teachings of German Offenlegungsschrift No. 2907460, employing a cyclosporin in accordance with the invention as the monocyclic peptide.

We claim:

1. A cyclosporin having a β-vinylene-α-amino acid residue at the 2-position and/or a β-hydroxy-α-amino acid residue at the 8-position.

2. A cyclosporin according to claim 1 of formula III,

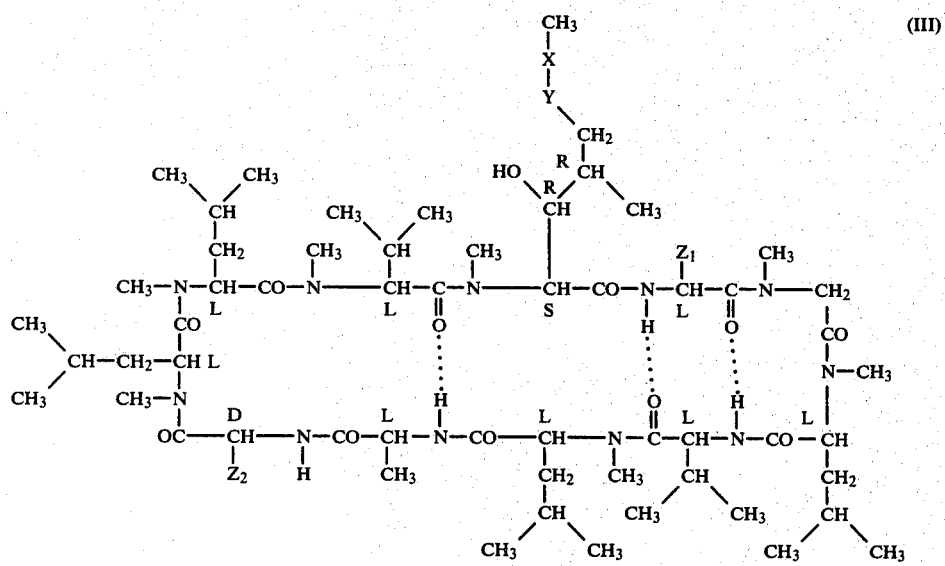

wherein
$Z_1$ is allyl or ethyl,
$Z_2$ is hydroxymethyl or, when $Z_1$ is allyl $Z_2$ is methyl, and
—X—Y— is —CH=CH— (trans) or —CH$_2$—CH$_2$—.

3. A cyclosporin according to claim 2, which is "(D)-Ser⑧-cyclosporin".

4. A cyclosporin according to claim 2, which is "(D)-Ser⑧-dihydrocyclosporin".

5. A cyclosporin according to claim 2, which is "Allylgly②-cyclosporin".

6. A pharmaceutical composition comprising an immunosuppressive effective amount of a cyclosporin according to claim 1 as active ingredient, together with a pharmaceutically acceptable diluent or carrier therefor.

7. A method of suppressing or reducing the immune response in a subject in need of such treatment, which method comprises administering to said subject an immunosuppressively effective amount of a cyclosporin according to claim 1.

8. A compound according to claim 1 in which the β-vinylene-α-amino acid residue is -Allylgly- and the β-hydroxy-α-amino acid residue is -(D)-Ser- or -(D)-Thr-.

9. A cyclosporin according to claim 1 of formula I

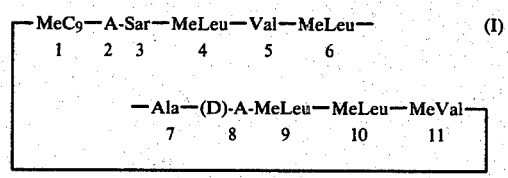

where
A is -Allylgly- or -α-Abu-,
(D)-A is -(D)-Ala-, -(D)-Ser- or -(D)-Thr-, and
MeC$_9$ is a residue of formula II

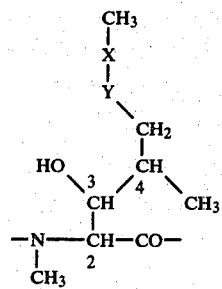

in which the positions 2, 3 and 4 have the configurations S,R and R respectively, and —X—Y— is —CH=CH— (trans) or —CH$_2$—CH$_2$—, with the proviso that when (D)-A is -(D)-Ala, A is -Allylgly-.

* * * * *